US006822125B2

(12) United States Patent
Lee et al.

(10) Patent No.: US 6,822,125 B2
(45) Date of Patent: Nov. 23, 2004

(54) METHOD FOR PREPARING DIMETHYLETHER USING A MEMBRANE REACTOR FOR SEPARATION AND REACTION

(75) Inventors: Kew-Ho Lee, Daejeon (KR); Bongkuk Sea, Daejeon (KR); Min Young Youn, Daejeon (KR); Dong-Wook Lee, Daegu (KR); Yoon-Gyu Lee, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 10/456,579

(22) Filed: Jun. 9, 2003

(65) Prior Publication Data

US 2004/0064002 A1 Apr. 1, 2004

(30) Foreign Application Priority Data

Sep. 26, 2002 (KR) .................................. 10-2002-58501

(51) Int. Cl.[7] .............................................. C07C 41/09
(52) U.S. Cl. ....................... 568/698; 568/699; 422/129; 422/239; 422/240
(58) Field of Search ............................. 568/698, 699; 422/129, 239, 240

(56) References Cited

U.S. PATENT DOCUMENTS 2,956,070 A * 10/1960 Jennings et al. ............ 554/170
4,035,430 A * 7/1977 Dwyer et al. ............... 585/322
5,935,533 A * 8/1999 Kleefisch et al. ........... 422/211
6,293,978 B2 * 9/2001 Kleefisch et al. ........... 48/198.2

OTHER PUBLICATIONS

Hsieh, H. P., "Inorganic Membranes For Separation And Reaction", Membrane Science and Technology Series 3, Elsevier, New York, pp. 299–366, (1996).

* cited by examiner

Primary Examiner—Rosalynd Keys
(74) Attorney, Agent, or Firm—Finnegan, Henderson, Farabow, Garrett & Dunner, LLP

(57) ABSTRACT

The present invention relates to a method for preparing dimethylether from methanol using a membrane reactor, more particularly to a method for preparing dimethylether from methanol using a membrane capable of carrying out a reaction and a separation at the same time while preparing dimethylether from methanol. Because water vapor generated by dehydration of methanol can be selectively removed from the catalytic reaction zone, decrease in catalytic activity can be prevented and thus life span of a catalyst can be extended. Further, reaction efficiency can be improved even at a temperature milder than the conventional one for dimethylether preparation, and also additional steps of separation and purification after completion of the reaction is no longer necessary.

5 Claims, 2 Drawing Sheets

A : Separation and Purification Process

Membrane Reactor

METHOD FOR PREPARING DIMETHYLETHER USING A MEMBRANE REACTOR FOR SEPARATION AND REACTION

BACKGROUND OF THE INVENTION

1. Field of the Invention

The present invention relates to a method for preparing dimethylether from methanol using a membrane reactor, more particularly to a method for preparing dimethylether from methanol using a membrane reactor which is capable of performing a reaction and a separation simultaneously. Since water vapor generated by catalytic reaction can be selectively removed from the reaction zone, decrease in catalytic activity can be prevented and thus a good reaction yield can be obtained even in a mild temperature condition. Further, no additional steps of dimethylether separation and purification are required.

2. Description of the Related Art

In manufacturing chemical products, the steps of a reaction and a separation take significant part of the process, which also requires enormous amount of energy-consumption. If a reaction and a separation steps can be carried out simultaneously using a membrane reactor, the resulting productivity can be much improved. Further, a membrane reactor can improve reaction yield by selectively removing specific substances generated during a reversible reaction with a membrane, thereby increasing conversion beyond thermodynamic equilibrium and reaction efficiency by inhibiting generation of by-products [H. P. Hsieh, "*Inorganic Membranes for Separation and Reaction*", Elsevier, N L, 1996].

The membrane technique is finding its use in various fields, including environmental and energy industries, chemical industries, biological industries and semiconductor industries, as a new technology enabling separation and purification with low energy consumption. Recently, development of a membrane reactor, which can greatly improve reaction yield by combination of reaction and separation steps, has been drawing much attention.

Dimethylether (DME), a prospective alternative fuel for a diesel engine, is being spotlighted as a clean transportation energy. At present, DME, the future clean fuel is produced from methanol in traditional catalyst reactors. DME emits much less nitrogen oxides than gasoline and diesel oils while having thermal efficiency still comparable to theirs. Also, it hardly causes smog and makes little noise. Accordingly, it is expected to be used in large scale as an alternative fuel for diesel oils and LPG, which account for more than 30% of the current transportation fuels in Korea. In this regard, establishment of an effective and stable mass-production system is drawing much attention. Production of dimethylether by dehydration of methanol can be represented by the following reaction formula.

$$2CH_3OH \leftrightarrows CH_3OCH_3 + H_2O$$

If a traditional catalyst reactor is used, the above reaction cannot proceed further once the reaction reaches thermodynamic equilibrium. Therefore, conversion of methanol and yield of DME are greatly limited. And, a complex distillation step, which consumes a lot of energy, is necessary to remove unreacted methanol and water vapor from the product to obtain high-purity DME. That is, the traditional method had to run the reactor at a high temperature of over 300° C. and a high pressure of over 10 atm to improve conversion and reaction yield. Water vapor generated during catalytic dehydration of methanol is known to decrease catalytic activity of alumina-silica catalyst. Therefore, improvement of catalytic reaction efficiency and simplification of process are required for a stable and effective DME mass-production system.

SUMMARY OF THE INVENTION

The inventors of the present invention have identified that when a membrane reactor capable of combining reaction and separation steps is used in preparation of DME from methanol, water vapor that may reduce catalytic activity can be selectively removed as soon as it is generated. Consequently, the life of a catalyst can be prolonged and reaction yield can be improved at a milder temperature and pressure condition compared to the conventional ones. Also, additional separation and purification steps are no longer required.

Accordingly, an object of the present invention is to provide a new membrane reactor capable of separating unreacted materials and impurities from a product and selectively removing them as soon as they are generated, and a method for preparing DME using the same.

DETAILED DESCRIPTION AND PREFERRED EMBODIMENTS

The present invention relates to a method for preparing dimethylether from methanol using a membrane reactor, which comprises: a step of injecting methanol into a reactor equipped with a membrane and filled with a catalyst; and a step of obtaining dimethylether simultaneously as water vapor generated by dehydration is separated by the membrane.

Hereinafter, the present invention is explained in more detail.

The present invention relates to a method for preparing dimethylether by dehydration of methanol using a membrane reactor capable of carrying out reaction and separation steps simultaneously. The membrane selectively removes water vapor generated by the catalytic reaction. Therefore, it prevents decrease of catalytic activity and prolongs catalyst life. And, a good reaction yield can be obtained in a mild temperature and pressure condition, and no additional separation and purification steps are required.

Hereinafter, the present invention is described more specifically.

Silica-alumina catalyst is filled into a reactor equipped with a membrane, and methanol is fed into the reactor. Although the kind of methanol to be used in the present invention is not particularly limited, the one with moisture content of lower than 5% will provide a more desirable result.

As the above membrane, a water vapor selective membrane made of ceramic or metal or a composite membrane of these is used. It is preferred that the membrane have water vapor permeability of 0.1 to 2.0 cc/cm$^2$·min. If the water vapor permeability is lower than 0.1 cc/cm$^2$·min, water vapor is removed too slow. In contrast, if it exceeds 2.0 cc/cm$^2$·min, methanol and DME are transmitted along with water vapor. It is preferred that the membrane have water vapor selectivity of 100 to 200. If the water vapor selectivity is below 100, it may lead to loss in methanol and DME. In contrast, if it exceeds 200, water vapor may not be sufficiently removed.

The conventional reactor that has been used for preparation of DME from methanol can be used, equipped with a membrane satisfying the above requirement. Such a reactor allows a mild temperature and pressure condition. That is, while the conventional reactor not equipped with a membrane normally requires 280 to 300° C. of a temperature condition, a membrane reactor of the present invention requires a temperature condition of 225 to 250° C., thereby much reducing energy consumption.

Figure 4:
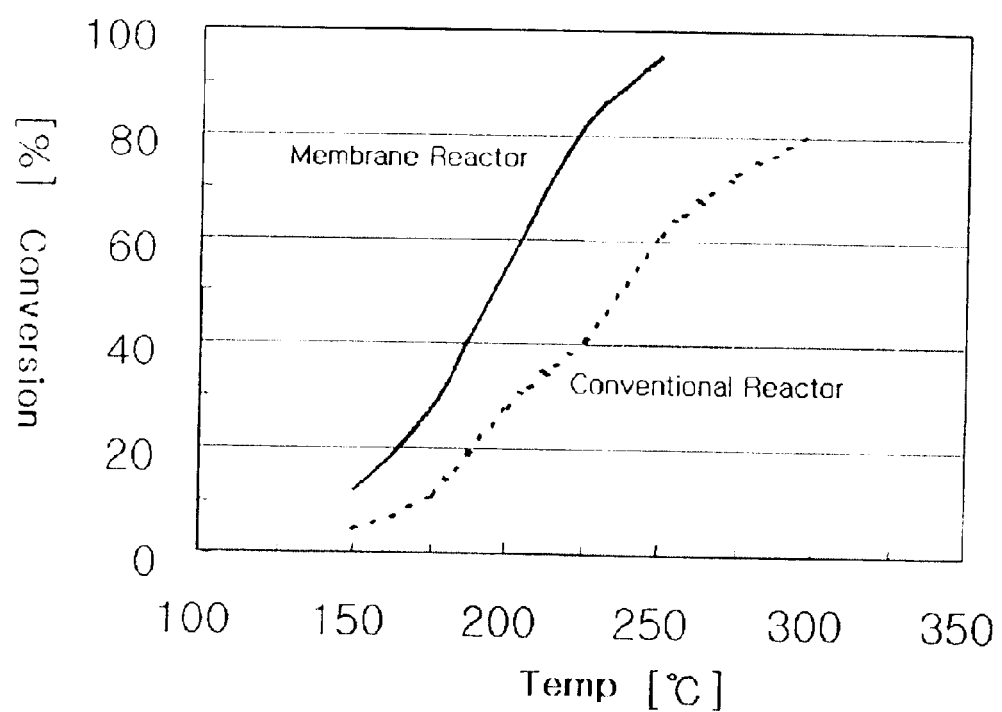
FIG. 4 is a graph that comparatively shows change in conversion depending on temperature between when a membrane reactor according to the present invention is used and when the conventional reactor is used.

In the above temperature range, methanol is dehydrated by a catalytic reaction to produce DME and water vapor. Then, the membrane selectively removes water vapor as soon as it is generated, thereby improving catalytic activity and increasing the catalyst's life. This is the most outstanding feature of the present invention. That is, in the conventional catalyst reactor, water vapor generated by dehydration of methanol is competitively adsorbed to a catalyst, thereby affecting reaction conversion and reaction yield, and at the same time, lowering catalytic activity. However, a membrane reactor of the present invention removes water vapor as soon as it is generated thereby improving catalytic reaction efficiency and catalytic activity. The dehydration of methanol and separation of water vapor by the membrane may both be carried out at 150°–300° C. and at 0.1–3.0 MPa. In general LHSV (liquid hourly space velocity) is determined as a parameter to measure the effect. A larger LHSV at the same reaction efficiency condition means increase of catalyst activity. FIG. 4 shows change in conversion depending on temperature between when a membrane reactor according to the present invention is used and when the conventional reactor is used.

The present invention can significantly decrease energy consumption by collecting DME and water vapor separately generated from methanol with one reactor, thus enabling to omit an additional step of removing water vapor. Also, Decrease in catalytic activity can be prevented since water vapor is removed as soon as it is generated. Therefore, it is expected that reaction conversion and reaction yield will be increased.

Further, a membrane reactor of the present invention can selectively separate products of a variety of reversible reactions. Therefore, it is very effective in improving equilibrium conversion and product purity. Also, productivity of chemical process can be improved since reaction and separation steps can be carried out simultaneously.

Hereinafter, the present invention is described in more detail with reference to the following Examples. However, the following Examples are only to be illustrative of the present invention, and the present invention should not be limited by the following Examples.

EXAMPLES

Examples 1 to 4

Preparation of Dimethylether Using a Membrane Reactor

Figure 1:
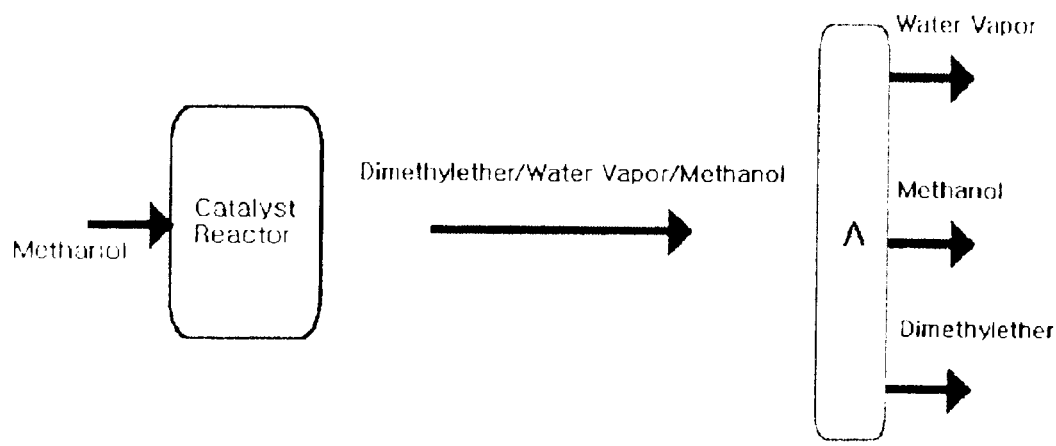
FIG. 1 shows reaction and separation steps of the conventional dimethylether preparation process.
Figure 2:
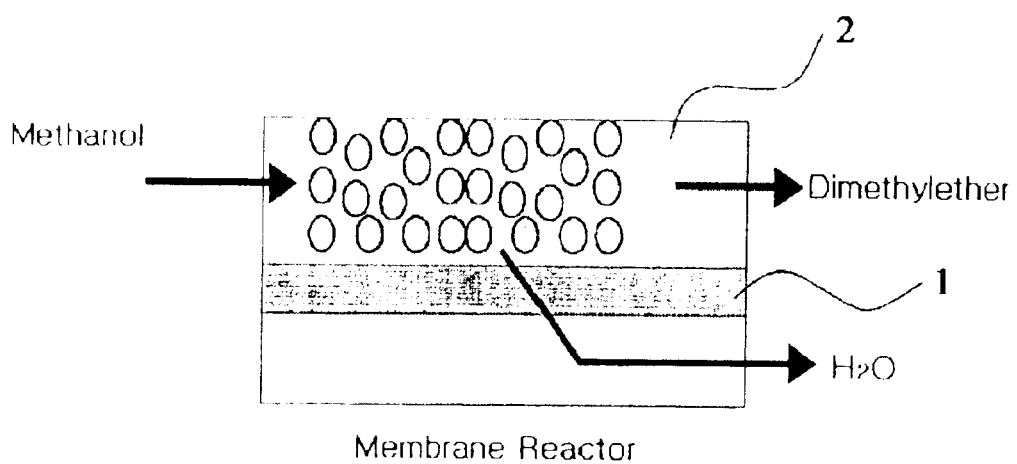
FIG. 2 shows dimethylether preparation process using a membrane reactor according to the present invention.
Figure 3:
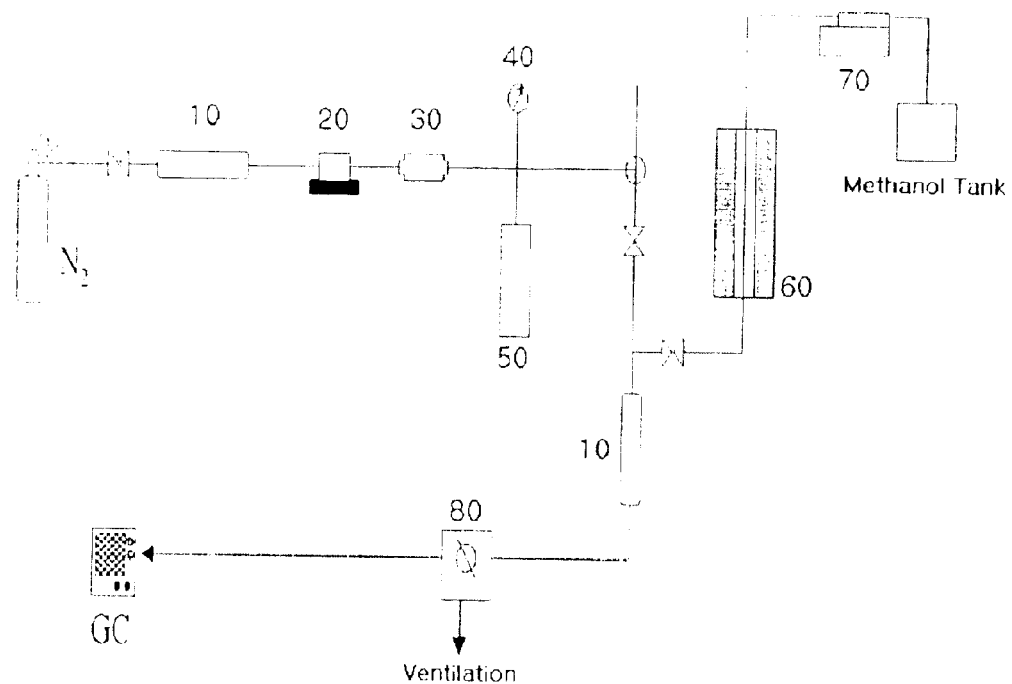
FIG. 3 shows a membrane reactor system according to the present invention.

Dimethylether (DME) was prepared from methanol using a tubular type membrane reactor made of SUS while varying reaction temperatures (225 to 300° C.) and methanol flow rates (LHSV; liquid hourly space velocity, 1.0 to 3.0/h) in order to find the best reaction condition. The reactor (outer diameter=½"; length=30 cm) was filled with alumina based catalyst for dehydration of methanol (50 to 70 meshes; silica-alumina catalyst; Aldrich) to about 1 cm of height. The reactor was equipped with a porous stainless steel/ceramic composite membrane capable of selectively transmitting and separating hot water vapor. The reactor was vertically fixed on a tubular furnace, and was heated at 350° C. for 4 hours under nitrogen atmosphere to activate the catalyst. Then, methanol was injected into the reactor along with nitrogen carrier gas using a HPLC pump. FIG. 3 shows the membrane reactor system used in the present invention. The reaction product was analyzed with GC using a Carbospher or Porapack T column.

Comparative Examples 1 to 2

Preparation of Dimethylether Using the Conventional Reactor

DME was prepared from methanol using a conventional tubular type fixed-bed reactor without a membrane. The reactor and reaction condition were the same as those of Examples 1 to 4. The result for the conventional reactor and the membrane reactor is shown in the following Table 1.

Experimental Example

Evaluation of Stability of the Membrane Reactor

Constant conversion and selectivity were obtained by running the reactor at 250° C. for 450 hours to evaluate stability of the membrane reactor. Transition ratio, selectivity (yield of DME) and LHSV, which are parameters for comparing the reaction systems, are defined as follows:

Methanol Conversion(%)=100×(moles of reacted methanol)/(moles of provided methanol)

Yield of *DME*(%)=100×(moles of produced *DME*)/(moles of provided methanol)

*LHSV*(h$^{-1}$)=[flow rate of methanol (g/h)]/[amount of catalyst(g)]

TABLE 1

| Classification | | Example 1 | Example 2 | Example 3 | Example 4 | Comp. Example 1 | Comp. Example 2 |
|---|---|---|---|---|---|---|---|
| Preparing Condition | Reaction temperature (° C.) | 225 | 225 | 250 | 250 | 280 | 300 |
| | LHSV (/h) | 1.6 | 2.4 | 1.6 | 2.4 | 1.6 | 1.6 |
| | Reaction pressure | 0.1 MPa | 0.1 MPa | 0.1 MPa | 01 MPa | 0.1 MPa | 0.1 MPa |

TABLE 1-continued

| | Classification | Example 1 | Example 2 | Example 3 | Example 4 | Comp. Example 1 | Comp. Example 2 |
|---|---|---|---|---|---|---|---|
| Result | Methanol Conversion (%) | 85 | 82 | 97 | 95 | 70 | 80 |
| | Yield of DME (%) | 92 | 90 | 99 | 96 | 80 | 85 |
| | Stability of catalytic activity | — | — | Over 450 hours | Over 450 hours | 100 hours | 100 hours |

Reaction catalysts used in Examples 1 to 4 and Comparative Examples 1 to 2 were Aldrich's alumina, alumina-silica and solid acid catalyst.

As shown in Table 1, the reactor of the present invention improved reaction conversion from 80% to 95%, and yield of DME from 85% to 95% in a milder temperature range of 225 to 250° C. Also, the life span of catalytic activity was prolonged more than four times. This is made possible because water vapor is removed by the membrane as soon as it is generated.

As described above, with the introduction of a reaction-separation combination type membrane reactor, dehydration of methanol and separation of water vapor can be carried out simultaneously during DME production. As a result, water vapor removal step can be omitted, and thus energy consumption can be decreased significantly. Also, because water vapor is removed as soon as it is generated, decrease in catalytic activity can be reduced, and methanol conversion and yield of DME increase.

Further, the membrane reactor of the present invention can be applied to various reversible reactions, as well as production of dimethylether, to selectively separate reaction products. The membrane reactor of the present invention is very effective in improving equilibrium conversion and product purity, and can increase productivity by combining reaction and separation steps.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A method for preparing dimethylether from methanol using a membrane reactor, which comprises:

injecting methanol into a reactor comprising a membrane and filled with a catalyst; and obtaining dimethylether simultaneously as water vapor generated by dehydration of methanol is separated by the membrane, wherein the membrane has a water vapor permeability ranging from 0.1 to 2.0 $cc/cm^2 \cdot min$ and a water vapor selectivity ranging from 100 to 200, the yield of dimethylether is at least 90%, and the methanol conversion is at least 82%.

2. The method for preparing dimethylether from methanol using a membrane reactor according to claim 1, wherein said dehydration and said separation of water vapor by the membrane are both carried out at 150–300° C. and 0.1–3.0 MPa.

3. The method for preparing dimethylether from methanol using a membrane reactor according to claim 1, wherein the membrane is selected from a group consisting of a ceramic membrane, a metal membrane and a composite membrane of metal and ceramic.

4. The method for preparing dimethylether from methanol using a membrane reactor according to claim 1, wherein moisture content of said methanol is less than 5%.

5. A membrane reactor for preparing dimethylether from methanol comprising a membrane that selectively separates product, reactant and by-product, the membrane having a water vapor permeability ranging from 0.1 to 2.0 $cc/cm^2$ min and a water vapor selectivity ranging from 100 to 200, wherein the membrane reactor is able to produce dimethylether yields of at least 90%, and methanol conversions of at least 82%.

* * * * *